US010112980B2

(12) United States Patent
Ander et al.

(10) Patent No.: US 10,112,980 B2
(45) Date of Patent: *Oct. 30, 2018

(54) MUTATED IMMUNOGLOBULIN-BINDING POLYPEPTIDES

(71) Applicant: GE Healthcare BioProcess R&D AB, Uppsala (SE)

(72) Inventors: Mats Ander, Uppsala (SE); Goran Bauren, Uppsala (SE); Tomas Bjorkman, Uppsala (SE); Gustav Rodrigo, Uppsala (SE)

(73) Assignee: GE HEALTHCARE BIOPROCESS R&D AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/598,685

(22) Filed: May 18, 2017

(65) Prior Publication Data

US 2017/0320922 A1    Nov. 9, 2017

Related U.S. Application Data (62) Division of application No. 14/904,077, filed as application No. PCT/SE2014/050882 on Jul. 10, 2014, now Pat. No. 9,663,558.

(30) Foreign Application Priority Data

Jul. 10, 2013 (SE) ...................................... 1350859
Jul. 10, 2013 (SE) ...................................... 1350860

(51) Int. Cl.

| C07K 14/31 | (2006.01) |
|---|---|
| C07K 14/745 | (2006.01) |
| C07K 16/00 | (2006.01) |
| C07K 1/22 | (2006.01) |
| B01D 15/38 | (2006.01) |
| B01J 20/32 | (2006.01) |
| B01J 20/286 | (2006.01) |

(52) U.S. Cl.
CPC .......... *C07K 14/31* (2013.01); *B01D 15/3809* (2013.01); *B01J 20/286* (2013.01); *B01J 20/3204* (2013.01); *B01J 20/3212* (2013.01); *B01J 20/3219* (2013.01); *B01J 20/3274* (2013.01); *C07K 1/22* (2013.01); *C07K 14/745* (2013.01); *C07K 16/00* (2013.01)

(58) Field of Classification Search
None
See application file for complete search history.

(56) References Cited

U.S. PATENT DOCUMENTS

| 6,602,977 | B1 | 8/2003 | Ljungqvist et al. | |
|---|---|---|---|---|
| 7,709,209 | B2 | 5/2010 | Hober et al. | |
| 9,382,297 | B2 | 7/2016 | Honda et al. | |
| 9,663,558 | B2 * | 5/2017 | Ander ................ | B01D 15/3809 |
| 2010/0221844 | A1 | 9/2010 | Bian et al. | |
| 2013/0046056 | A1 | 2/2013 | Spector et al. | |
| 2016/0134072 | A1 | 5/2016 | Faber et al. | |

FOREIGN PATENT DOCUMENTS

| CN | 101775069 | A | | 7/2010 |
|---|---|---|---|---|
| EP | 2202310 | A2 | | 6/2010 |
| EP | 3019519 | A1 | | 5/2016 |
| JP | 2002542259 | A | | 12/2002 |
| JP | 2005538693 | A | | 12/2005 |
| JP | 2010081866 | A | | 4/2010 |
| JP | 2010156687 | A | | 7/2010 |
| JP | 2016525329 | A | | 8/2016 |
| WO | 2000/063243 | A1 | | 10/2000 |
| WO | 0063243 | | * | 10/2000 |
| WO | 2011/005341 | A2 | | 1/2011 |
| WO | 2012/087231 | A1 | | 6/2012 |
| WO | 2012083425 | A1 | | 6/2012 |
| WO | 2012/165544 | A1 | | 12/2012 |
| WO | 2012165544 | | * | 12/2012 |
| WO | 2015/005862 | A1 | | 1/2015 |

OTHER PUBLICATIONS

Supplementary European Search Report from European Patent Application No. 14823321 dated Feb. 2, 2017.
International Search Report and Written Opinion Received for PCT Application No. PCT/SE2014/050882 dated Oct. 14, 2014, 13 Pages.
International Preliminary Report on Patentability Received for PCT Application No. PCT/SE2014/050882 dated Jan. 12, 2016, 8 Pages.
Chinese Office Action and Search Report Received for Chinese Patent Application 201480039292.8 dated Aug. 3, 2018, 11 pages (English Translation).

* cited by examiner

*Primary Examiner* — Maury A Audet
(74) *Attorney, Agent, or Firm* — Wood IP LLC (57) ABSTRACT

The invention discloses a polypeptide with improved alkaline stability, which polypeptide comprises a mutant of a B or C domain of Staphylococcus Protein A (SpA), as specified by SEQ ID NO 1 or SEQ ID NO 2, or of Protein Z, as specified by SEQ ID NO 3, wherein at least the glutamic acid residue at position 15 has been mutated to an amino acid other than asparagine. The invention also discloses multimers of said polypeptide, as well as separation matrices comprising the multimers or polypeptides.

25 Claims, 1 Drawing Sheet

Specification includes a Sequence Listing.

SEQUENCE LISTING

<160> NUMBER OF SEQ ID NOS: 13

<210> SEQ ID NO 1
<211> LENGTH: 58
<212> TYPE: PRT
<213> ORGANISM: Staphylococcus aureus

<400> SEQUENCE: 1

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 2
<211> LENGTH: 58
<212> TYPE: PRT
<213> ORGANISM: Staphylococcus aureus

<400> SEQUENCE: 2

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
         35                  40                  45

Lys Lys Leu Asn Asp Ala Gln Ala Pro Lys
 50                  55

<210> SEQ ID NO 3
<211> LENGTH: 58
<212> TYPE: PRT
<213> ORGANISM: Escherichia coli

<400> SEQUENCE: 3

Val Asp Asn Lys Phe Asn Lys Glu Gln Gln Asn Ala Phe Tyr Glu Ile
 1               5                  10                  15

Leu His Leu Pro Asn Leu Asn Glu Glu Gln Arg Asn Ala Phe Ile Gln
             20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys
 50                  55

<210> SEQ ID NO 4
<211> LENGTH: 58
<212> TYPE: PRT
<213> ORGANISM: Escherichia coli

<400> SEQUENCE: 4

Val Asp Ala Lys Phe Asp Lys Glu Gln Gln Asn Ala Phe Tyr Glu Ile
 1               5                  10                  15

Leu His Leu Pro Asn Leu Thr Glu Glu Gln Arg Asn Ala Phe Ile Gln
             20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys
 50                  55

<210> SEQ ID NO 5
<211> LENGTH: 58
<212> TYPE: PRT
<213> ORGANISM: Escherichia coli

<400> SEQUENCE: 5

Val Asp Asn Lys Phe Asn Lys Glu Gln Gln Asn Ala Phe Tyr Glu Ile
 1               5                  10                  15

Leu His Leu Pro Asn Leu Thr Glu Glu Gln Arg Asn Ala Phe Ile Gln
             20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys
 50                  55

<210> SEQ ID NO 6
<211> LENGTH: 58
<212> TYPE: PRT
<213> ORGANISM: Escherichia coli

<400> SEQUENCE: 6

Val Asp Ala Lys Phe Asp Lys Glu Ala Gln Asn Ala Phe Tyr Lys Ile
 1               5                  10                  15

Leu His Leu Pro Asn Leu Thr Glu Glu Gln Arg Asn Ala Phe Ile Gln
             20                  25                  30

```
Ser Leu Lys Asp Asp Pro Ser Gln Ser Ala Asn Leu Leu Ala Glu Ala
        35                  40                  45

Lys Lys Leu Asn Asp Ala Gln Ala Pro Lys
 50                  55
```

<210> SEQ ID NO 7
<211> LENGTH: 58
<212> TYPE: PRT
<213> ORGANISM: Escherichia coli

<400> SEQUENCE: 7

```
Val Asp Ala Lys Phe Asp Lys Glu Ala Gln Asn Ala Phe Tyr Glu Ile
 1               5                  10                  15

Leu His Leu Pro Asn Leu Thr Glu Glu Gln Arg Asn Ala Phe Ile Gln
                20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
 50                  55
```

<210> SEQ ID NO 8
<211> LENGTH: 58
<212> TYPE: PRT
<213> ORGANISM: Escherichia coli

<400> SEQUENCE: 8

```
Val Asp Ala Lys Phe Asp Lys Glu Ala Gln Asn Ala Phe Tyr Lys Ile
 1               5                  10                  15

Leu His Leu Pro Asn Leu Thr Glu Glu Gln Arg Asn Ala Phe Ile Gln
                20                  25                  30

Ser Leu Lys Thr Asp Pro Ser Val Ser Lys Asn Ile Leu Ala Ala Ala
        35                  40                  45

Lys Lys Leu Asn Asp Ala Gln Ala Pro Lys
 50                  55
```

<210> SEQ ID NO 9
<211> LENGTH: 58
<212> TYPE: PRT
<213> ORGANISM: Escherichia coli

<400> SEQUENCE: 9

```
Val Asp Asn Lys Phe Asn Lys Glu Ala Gln Asn Ala Phe Tyr Lys Ile
 1               5                  10                  15

Leu His Leu Pro Asn Leu Thr Glu Glu Gln Arg Asn Ala Phe Ile Gln
                20                  25                  30

Ser Leu Lys Thr Asp Pro Ser Val Ser Lys Asn Ile Leu Ala Ala Ala
        35                  40                  45

Lys Lys Leu Asn Asp Ala Gln Ala Pro Lys
 50                  55
```

<210> SEQ ID NO 10
<211> LENGTH: 58
<212> TYPE: PRT
<213> ORGANISM: Escherichia coli

<400> SEQUENCE: 10

```
Val Asp Asn Lys Phe Asn Lys Glu Ala Gln Asn Ala Phe Tyr Lys Ile
 1               5                  10                  15

Leu His Leu Pro Asn Leu Thr Glu Glu Gln Arg Ala Ala Phe Ile Gln
                20                  25                  30
```

```
Ser Leu Lys Thr Asp Pro Ser Val Ser Lys Asn Ile Leu Ala Ala Ala
        35                  40                  45

Lys Lys Leu Asn Asp Ala Gln Ala Pro Lys
 50                  55
```

<210> SEQ ID NO 11
<211> LENGTH: 235
<212> TYPE: PRT
<213> ORGANISM: Escherichia coli

<400> SEQUENCE: 11

```
Ala Gln Val Asp Ala Lys Phe Asp Lys Glu Gln Gln Asn Ala Phe Tyr
 1               5                  10                  15

Glu Ile Leu His Leu Pro Asn Leu Thr Glu Glu Gln Arg Asn Ala Phe
            20                  25                  30

Ile Gln Ser Leu Lys Asp Asp Pro Ser Gln Ser Ala Asn Leu Leu Ala
        35                  40                  45

Glu Ala Lys Lys Leu Asn Asp Ala Gln Ala Pro Lys Val Asp Ala Lys
 50                  55                  60

Phe Asp Lys Glu Gln Gln Asn Ala Phe Tyr Glu Ile Leu His Leu Pro
 65                  70                  75                  80

Asn Leu Thr Glu Glu Gln Arg Asn Ala Phe Ile Gln Ser Leu Lys Asp
                85                  90                  95

Asp Pro Ser Gln Ser Ala Asn Leu Leu Ala Glu Ala Lys Lys Leu Asn
            100                 105                 110

Asp Ala Gln Ala Pro Lys Val Asp Ala Lys Phe Asp Lys Glu Gln Gln
        115                 120                 125

Asn Ala Phe Tyr Glu Ile Leu His Leu Pro Asn Leu Thr Glu Glu Gln
130                 135                 140

Arg Asn Ala Phe Ile Gln Ser Leu Lys Asp Asp Pro Ser Gln Ser Ala
145                 150                 155                 160

Asn Leu Leu Ala Glu Ala Lys Lys Leu Asn Asp Ala Gln Ala Pro Lys
                165                 170                 175

Val Asp Ala Lys Phe Asp Lys Glu Gln Gln Asn Ala Phe Tyr Glu Ile
            180                 185                 190

Leu His Leu Pro Asn Leu Thr Glu Glu Gln Arg Asn Ala Phe Ile Gln
        195                 200                 205

Ser Leu Lys Asp Asp Pro Ser Gln Ser Ala Asn Leu Leu Ala Glu Ala
210                 215                 220

Lys Lys Leu Asn Asp Ala Gln Ala Pro Lys Cys
225                 230                 235
```

<210> SEQ ID NO 12
<211> LENGTH: 235
<212> TYPE: PRT
<213> ORGANISM: Escherichia coli

<400> SEQUENCE: 12

```
Ala Gln Val Asp Ala Lys Phe Asp Lys Glu Ala Gln Asn Ala Phe Tyr
 1               5                  10                  15

Glu Ile Leu His Leu Pro Asn Leu Thr Glu Gln Gln Arg Asn Ala Phe
            20                  25                  30

Ile Gln Ser Leu Lys Asp Asp Pro Ser Gln Ser Ala Asn Leu Leu Ala
        35                  40                  45

Glu Ala Lys Lys Leu Asn Asp Ala Gln Ala Pro Lys Val Asp Ala Lys
 50                  55                  60
```

```
Phe Asp Lys Glu Ala Gln Asn Ala Phe Tyr Glu Ile Leu His Leu Pro
 65                  70                  75                  80

Asn Leu Thr Glu Glu Gln Arg Asn Ala Phe Ile Gln Ser Leu Lys Asp
                 85                  90                  95

Asp Pro Ser Gln Ser Ala Asn Leu Leu Ala Glu Ala Lys Lys Leu Asn
            100                 105                 110

Asp Ala Gln Ala Pro Lys Val Asp Ala Lys Phe Asp Lys Glu Ala Gln
        115                 120                 125

Asn Ala Phe Tyr Glu Ile Leu His Leu Pro Asn Leu Thr Glu Glu Gln
    130                 135                 140

Arg Asn Ala Phe Ile Gln Ser Leu Lys Asp Asp Pro Ser Gln Ser Ala
145                 150                 155                 160

Asn Leu Leu Ala Glu Ala Lys Lys Leu Asn Asp Ala Gln Ala Pro Lys
                165                 170                 175

Val Asp Ala Lys Phe Asp Lys Glu Ala Gln Asn Ala Phe Tyr Glu Ile
            180                 185                 190

Leu His Leu Pro Asn Leu Thr Glu Glu Gln Arg Asn Ala Phe Ile Gln
        195                 200                 205

Ser Leu Lys Asp Asp Pro Ser Gln Ser Ala Asn Leu Leu Ala Glu Ala
    210                 215                 220

Lys Lys Leu Asn Asp Ala Gln Ala Pro Lys Cys
225                 230                 235

<210> SEQ ID NO 13
<211> LENGTH: 235
<212> TYPE: PRT
<213> ORGANISM: Escherichia coli

<400> SEQUENCE: 13

Ala Gln Val Asp Ala Lys Phe Asp Lys Glu Ala Gln Asn Ala Phe Tyr
  1               5                  10                  15

Lys Ile Leu His Leu Pro Asn Leu Thr Glu Glu Gln Arg Asn Ala Phe
                 20                  25                  30

Ile Gln Ser Leu Lys Asp Asp Pro Ser Gln Ser Ala Asn Leu Leu Ala
            35                  40                  45

Glu Ala Lys Lys Leu Asn Asp Ala Gln Ala Pro Lys Val Asp Ala Lys
         50                  55                  60

Phe Asp Lys Glu Ala Gln Asn Ala Phe Tyr Lys Ile Leu His Leu Pro
 65                  70                  75                  80

Asn Leu Thr Glu Glu Gln Arg Asn Ala Phe Ile Gln Ser Leu Lys Asp
                 85                  90                  95

Asp Pro Ser Gln Ser Ala Asn Leu Leu Ala Glu Ala Lys Lys Leu Asn
            100                 105                 110

Asp Ala Gln Ala Pro Lys Val Asp Ala Lys Phe Asp Lys Glu Ala Gln
        115                 120                 125

Asn Ala Phe Tyr Lys Ile Leu His Leu Pro Asn Leu Thr Glu Glu Gln
    130                 135                 140

Arg Asn Ala Phe Ile Gln Ser Leu Lys Asp Asp Pro Ser Gln Ser Ala
145                 150                 155                 160

Asn Leu Leu Ala Glu Ala Lys Lys Leu Asn Asp Ala Gln Ala Pro Lys
                165                 170                 175

Val Asp Ala Lys Phe Asp Lys Glu Ala Gln Asn Ala Phe Tyr Lys Ile
            180                 185                 190

Leu His Leu Pro Asn Leu Thr Glu Glu Gln Arg Asn Ala Phe Ile Gln
        195                 200                 205
```

-continued

```
Ser Leu Lys Asp Asp Pro Ser Gln Ser Ala Asn Leu Leu Ala Glu Ala
    210                 215                 220

Lys Lys Leu Asn Asp Ala Gln Ala Pro Lys Cys
225                 230                 235
```

MUTATED IMMUNOGLOBULIN-BINDING POLYPEPTIDES

CROSS REFERENCE TO RELATED APPLICATIONS

This application is a divisional application of U.S. application Ser. No. 14/904,077 filed on Jan. 8, 2016, which will issue as U.S. Pat. No. 9,663,558 on May 30, 2017, which is a filing under 35 U.S.C. § 371 and claims priority to international patent application number PCT/SE2014/050882 filed on Jul. 10, 2014, which claims priority to patent application numbers 1350859-3 and 1350860-1, both filed in Sweden on Jul. 10, 2013, all of which are incorporated herein by reference.

STATEMENT REGARDING SEQUENCE LISTING

The Sequence Listing associated with this application is part of the description and is provided in text the form of an Annex C/ST.25 text file in lieu of a paper copy, and is hereby incorporated by reference into the specification. The name of the text file containing the Sequence Listing is 266175A_8_DIV1_SequenceListing.txt. The text file is 13 kb, was created on May 18, 2017, and is being submitted herewith electronically via EFS-Web.

TECHNICAL FIELD OF THE INVENTION

Embodiments of the present invention relate to the field of affinity chromatography, and more specifically to mutated immunoglobulin-binding domains of Protein A, which are useful in affinity chromatography of immunoglobulins. Embodiments of the present invention also relate to multimers of the mutated domains and to separation matrices containing the mutated domains or multimers.

BACKGROUND OF THE INVENTION

Immunoglobulins represent the most prevalent biopharmaceutical products in either manufacture or development worldwide. The high commercial demand for and hence value of this particular therapeutic market has led to the emphasis being placed on pharmaceutical companies to maximize the productivity of their respective mAb manufacturing processes whilst controlling the associated costs.

Affinity chromatography is used in most cases, as one of the key steps in the purification of these immunoglobulin molecules, such as monoclonal or polyclonal antibodies. A particularly interesting class of affinity reagents is proteins capable of specific binding to invariable parts of an immunoglobulin molecule, such interaction being independent on the antigen-binding specificity of the antibody. Such reagents can be widely used for affinity chromatography recovery of immunoglobulins from different samples such as but not limited to serum or plasma preparations or cell culture derived feed stocks. An example of such a protein is staphylococcal protein A, containing domains capable of binding to the Fc and Fab portions of IgG immunoglobulins from different species.

Staphylococcal protein A (SpA) based reagents have due to their high affinity and selectivity found a widespread use in the field of biotechnology, e.g. in affinity chromatography for capture and purification of antibodies as well as for detection or quantification. At present, SpA-based affinity medium probably is the most widely used affinity medium for isolation of monoclonal antibodies and their fragments from different samples including industrial cell culture supernatants. Accordingly, various matrices comprising protein A-ligands are commercially available, for example, in the form of native protein A (e.g. Protein A SEPHAROSE™, GE Healthcare, Uppsala, Sweden) and also comprised of recombinant protein A (e.g. rProtein A-SEPHAROSE™, GE Healthcare). More specifically, the genetic manipulation performed in the commercial recombinant protein A product is aimed at facilitating the attachment thereof to a support.

These applications, like other affinity chromatography applications, require comprehensive attention to definite removal of contaminants. Such contaminants can for example be non-eluted molecules adsorbed to the stationary phase or matrix in a chromatographic procedure, such as non-desired biomolecules or microorganisms, including for example proteins, carbohydrates, lipids, bacteria and viruses. The removal of such contaminants from the matrix is usually performed after a first elution of the desired product in order to regenerate the matrix before subsequent use. Such removal usually involves a procedure known as cleaning-in-place (CIP), wherein agents capable of eluting contaminants from the stationary phase are used. One such class of agents often used is alkaline solutions that are passed over the stationary phase. At present the most extensively used cleaning and sanitizing agent is NaOH, and the concentration thereof can range from 0.1 up to e.g. 1 M, depending on the degree and nature of contamination. This strategy is associated with exposing the matrix for pH-values above 13. For many affinity chromatography matrices containing proteinaceous affinity ligands such alkaline environment is a very harsh condition and consequently results in decreased capacities owing to instability of the ligand to the high pH involved.

An extensive research has therefore been focused on the development of engineered protein ligands that exhibit an improved capacity to withstand alkaline pH-values. For example, Gülich et al. (Susanne Gülich, Martin Linhult, Per-Åke Nygren, Mathias Uhlén, Sophia Hober, Journal of Biotechnology 80 (2000), 169-178) suggested protein engineering to improve the stability properties of a Streptococcal albumin-binding domain (ABD) in alkaline environments. Gülich et al. created a mutant of ABD, wherein all the four asparagine residues have been replaced by leucine (one residue), aspartate (two residues) and lysine (one residue). Further, Gülich et al. report that their mutant exhibits a target protein binding behavior similar to that of the native protein, and that affinity columns containing the engineered ligand show higher binding capacities after repeated exposure to alkaline conditions than columns prepared using the parental non-engineered ligand. Thus, it is concluded therein that all four asparagine residues can be replaced without any significant effect on structure and function.

Recent work shows that changes can also be made to protein A (SpA) to effect similar properties. US patent application publication US 2005/0143566 discloses that when at least one asparagine residue is mutated to an amino acid other than glutamine or aspartic acid, the mutation confers an increased chemical stability at pH-values of up to about 13-14 compared to the parental SpA, such as the B-domain of SpA, or Protein Z, a synthetic construct derived from the B-domain of SpA (U.S. Pat. No. 5,143,844). The authors show that when these mutated proteins are used as affinity ligands, the separation media as expected can better withstand cleaning procedures using alkaline agents. Further mutations of protein A domains with the purpose of increasing the alkali stability have also been published in WO 2008/039141, JP 2006304633A, EP 1992692A1, EP2202310A2, WO 2010/110288, WO 2012/086660 and WO 2012/083425. However, the currently available mutations are still sensitive to alkaline pH and the NaOH concentration during cleaning is usually limited to 0.1 M, which means that complete cleaning is difficult to achieve. Higher NaOH concentrations, which would improve the cleaning, lead to unacceptable capacity losses.

There is thus still a need in this field to obtain a separation matrix containing protein ligands having a further improved stability towards alkaline cleaning procedures.

SUMMARY OF THE INVENTION

One aspect of the invention is to provide a polypeptide with improved alkaline stability. This is achieved with a polypeptide.

One benefit is that the alkaline stability is improved over the parental polypeptides. Another benefit is a highly selective binding towards immunoglobulins and other Fc-containing proteins.

A second aspect of the invention is to provide a multimer with improved alkaline stability, comprising a plurality of polypeptides. This is achieved with a multimer as defined in the claims.

A third aspect of the invention is to provide a nucleic acid or a vector encoding a polypeptide or multimer with improved alkaline stability. This is achieved with a nucleic acid or vector as defined in the claims.

A fourth aspect of the invention is to provide an expression system capable of expressing a polypeptide or multimer with improved alkaline stability. This is achieved with an expression system as defined in the claims.

A fifth aspect of the invention is to provide a separation matrix capable of selectively binding immunoglobulins and other Fc-containing proteins and exhibiting an improved alkaline stability. This is achieved with a separation matrix as defined in the claims.

A sixth aspect of the invention is to provide an efficient and economical method of isolating an immunoglobulin or other Fc-containing protein. This is achieved with a method as defined in the claims.

Further suitable embodiments of the invention are described in the dependent claims.

Definitions

The terms "antibody" and "immunoglobulin" are used interchangeably herein, and are understood to include also fragments of antibodies, fusion proteins comprising antibodies or antibody fragments and conjugates comprising antibodies or antibody fragments.

The terms an "Fc-binding polypeptide" and "Fc-binding protein" mean a polypeptide or protein respectively, capable of binding to the crystallisable part (Fc) of an antibody and includes e.g. Protein A and Protein G, or any fragment or fusion protein thereof that has maintained the binding property.

DETAILED DESCRIPTION OF THE INVENTION

In one aspect the present invention discloses a polypeptide, which comprises, or consists essentially of, a mutant of a B or C domain of Staphylococcus Protein A (SpA), as specified by SEQ ID NO 1 or SEQ ID NO 2, or of Protein Z, as specified by SEQ ID NO 3 or SEQ ID NO 4, wherein at least the glutamic acid residue at position 15 has been mutated to an amino acid other than asparagine or glutamine. SEQ ID NO 4 denotes a variant of Protein Z, with the mutations N3A, N6D, N23T. The mutation of E15 in these domains confers an improved alkali stability in comparison with the parental domain/polypeptide, without impairing the immunoglobulin-binding properties. Hence, the polypeptide can also be described as an Fc- or immunoglobulin-binding polypeptide.

```
(SpA B domain)
                                     SEQ ID NO 1
ADNKFNKEQQ NAFYEILHLP NLNEEQRNGF IQSLKDDPSQ

SANLLAEAKK LNDAQAPK (SpA C domain)
                                     SEQ ID NO 2
ADNKFNKEQQ NAFYEILHLP NLTEEQRNGF IQSLKDDPSV

SKEILAEAKK LNDAQAPK (Protein Z)
                                     SEQ ID NO 3
VDNKFNKEQQ NAFYEILHLP NLNEEQRNAF IQSLKDDPSQ

SANLLAEAKK LNDAQAPK (Zvar)
                                     SEQ ID NO 4
VDAKFDKEQQ NAFYEILHLP NLTEEQRNAF IQSLKDDPSQ

SANLLAEAKK LNDAQAPK
```

In certain embodiments, at least the glutamic acid residue at position 15 has been mutated to an amino acid other than asparagine, proline or cysteine. In particular embodiments the glutamic acid residue at position 15 has been mutated to a lysine. This has the unexpected advantage that the alkali stability is improved. The E15 mutation (e.g. a E15K mutation) may be the only mutation or the polypeptide may also comprise further mutations, such as in at least one of the N3, N6, Q9, Q10, H18, N21, N23, N28, G/A29, D36, Q/V40, A/K42, N/E43, L/I44, E47, Q55 and P57 positions. In one or more of these positions, the original amino acid residue may e.g. be substituted with an amino acid which is not asparagine, proline or cysteine. The original amino acid residue may e.g. be substituted with an alanine, a valine, a threonine, a serine, a lysine or an aspartic acid.

In some embodiments, the amino acid residue at position 23 is a threonine or an alanine.

In certain embodiments, the amino acid residue at position 3 is an alanine and/or the amino acid residue at position 6 is an aspartic acid. In certain embodiments, at least one of the amino acid residues at position 3 and 6 is an asparagine.

In some embodiments, the serine residue at position 33 has been mutated to an amino acid other than asparagine, glutamine, proline or cysteine, such as to a lysine. In alternative embodiments, the amino acid residue at position 33 is a serine.

In certain embodiments, the glutamine residue at position 9 has been mutated to an amino acid other than asparagine, glutamine, proline or cysteine, such as to an alanine. The mutation at position 9 has in itself an effect of improving the alkali stability, but the stability is further improved by the E15 mutation, such as an E15K mutation.

In some embodiments, the glutamine residue at position 10 has been mutated to an amino acid other than asparagine, glutamine, proline or cysteine, such as to an alanine. In alternative embodiments, the amino acid residue at position 10 is a glutamine.

In certain embodiments, the glutamine residue at position 32 has been mutated to an amino acid other than asparagine, glutamine, proline or cysteine, such as to an alanine. In alternative embodiments, the amino acid residue at position 32 is a glutamine.

In some embodiments, the glutamine residue at position 40 has been mutated to an amino acid other than asparagine, glutamine, proline or cysteine, such as to an alanine or valine. In alternative embodiments, the amino acid residue at position 40 is a glutamine.

In certain embodiments, the glutamine residue at position 55 has been mutated to an amino acid other than asparagine, glutamine, proline or cysteine, such as to an alanine, a serine or glutamic acid. In alternative embodiments, the amino acid residue at position 55 is a glutamine.

In some embodiments, the amino acid residue at position 26 is a glutamine. In alternative embodiments, the glutamine at position 26 has been mutated to an amino acid other than asparagine, glutamine, proline or cysteine.

In some embodiments, the glutamic acid residue at position 47 has been mutated to an amino acid other than asparagine, glutamine, proline or cysteine, such as to an alanine or a threonine. In alternative embodiments, the amino acid residue at position 47 is a glutamic acid.

In certain embodiments, the asparagine residue at position 21 has been mutated to an amino acid other than glutamine, proline or cysteine, such as to an aspartic acid. In alternative embodiments, the amino acid residue at position 21 is an asparagine.

In certain embodiments, the aspartic acid residue at position 36 has been mutated to an amino acid other than glutamine, proline or cysteine. In particular embodiments, the aspartic acid residue at position 36 has been mutated to an alanine or a threonine. In alternative embodiments, the amino acid at position 36 is an aspartic acid.

In some embodiments, the mutation is Q9A, E15K. This mutation provides particularly high alkaline stabilities. In certain embodiments, the polypeptide comprises a sequence selected from the group consisting of SEQ ID NO 6, SEQ ID NO 8, SEQ ID NO 9 and SEQ ID NO 10 and additionally SEQ ID NO 13. The polypeptide may e.g. be defined by SEQ ID NO 6, or 8-10, but it may also comprise additional amino acid residues at the C- and/or N-terminal end.

```
Zvar(Q9A, E15K)
                                             SEQ ID NO 6
VDAKFDKEAQ NAFYKILHLP NLTEEQRNAF IQSLKDDPSQ

SANLLAEAKK LNDAQAPK

SEQ ID NO 8
VDAKFDKEAQ NAFYKILHLP NLTEEQRNAF IQSLKTDPSV

SKNILAAAKK LNDAQAPK

SEQ ID NO 9
VDNKFNKEAQ NAFYKILHLP NLTEEQRNAF IQSLKTDPSV

SKNILAAAKK LNDAQAPK

SEQ ID NO 10
VDNKFNKEAQ NAFYKILHLP NLTEEQRAAF IQSLKTDPSV

SKNILAAAKK LNDAQAPK

Zvar4
                                             SEQ ID No 11
AQ VDAKFDKEQQ NAFYEILHLP NLTEEQRNAF IQSLKDDPSQ

SANLLAEAKK LNDAQAPK VDAKFDKEQQ NAFYEILHLP

NLTEEQRNAF IQSLKDDPSQ SANLLAEAKK LNDAQAPK

VDAKFDKEQQ NAFYEILHLP NLTEEQRNAF IQSLKDDPSQ

SANLLAEAKK LNDAQAPK VDAKFDKEQQ NAFYEILHLP

NLTEEQRNAF IQSLKDDPSQ SANLLAEAKK LNDAQAPKC

Zvar(Q9A)4
                                             SEQ ID NO 12
AQ VDAKFDKEAQ NAFYEILHLP NLTEEQRNAF IQSLKDDPSQ

SANLLAEAKK LNDAQAPK VDAKFDKEAQ NAFYEILHLP

NLTEEQRNAF IQSLKDDPSQ SANLLAEAKK LNDAQAPK

VDAKFDKEAQ NAFYEILHLP NLTEEQRNAF IQSLKDDPSQ

SANLLAEAKK LNDAQAPK VDAKFDKEAQ NAFYEILHLP

NLTEEQRNAF IQSLKDDPSQ SANLLAEAKK LNDAQAPKC

Zvar(Q9A, E15K)4
                                             SEQ ID NO 13
AQ VDAKFDKEAQ NAFYKILHLP NLTEEQRNAF IQSLKDDPSQ

SANLLAEAKK LNDAQAPK VDAKFDKEAQ NAFYKILHLP

NLTEEQRNAF IQSLKDDPSQ SANLLAEAKK LNDAQAPK

VDAKFDKEAQ NAFYKILHLP NLTEEQRNAF IQSLKDDPSQ

SANLLAEAKK LNDAQAPK VDAKFDKEAQ NAFYKILHLP

NLTEEQRNAF IQSLKDDPSQ SANLLAEAKK LNDAQAPKC
```

In a second aspect the present invention discloses a multimer comprising, or consisting essentially of, a plurality of polypeptide units as defined by any embodiment disclosed above. The multimer can e.g. be a dimer, a trimer, a tetramer, a pentamer or a hexamer. It can be a homomultimer, where all the units in the multimer are identical or it can be a heteromultimer, where at least one unit differs from the others. Advantageously, all the units in the multimer are alkali stable, such as by comprising the mutations disclosed above. The polypeptides can be linked to each directly by peptide bonds between the C-terminal and N-terminal ends of the polypeptides. Alternatively, two or more units in the multimer can be linked by elements comprising oligomeric or polymeric species, such as elements comprising up to 15 or 30 amino acids, such as 1-5, 1-10 or 5-10 amino acids. The nature of such a link should preferably not destabilize the spatial conformation of the protein units. This can e.g. be achieved by avoiding the presence of proline in the links. Furthermore, said link should preferably also be sufficiently stable in alkaline environments not to impair the properties of the mutated protein units. For this purpose, it is advantageous if the links do not contain asparagine. It can additionally be advantageous if the links do not contain glutamine. The multimer may further at the N-terminal end comprise a plurality of amino acid residues originating from the cloning process or constituting a residue from a cleaved off signaling sequence. The number of additional amino acid residues may e.g. be 15 or less, such as 10 or less or 5 or less.

As a specific example, the multimer may comprise an AQ sequence at the N-terminal end as in SEQ ID NO 13.

In some embodiments, the polypeptide and/or multimer, as disclosed above, further comprises at the C-terminal or N-terminal end one or more coupling elements, selected from the group consisting of a cysteine residue, a plurality of lysine residues and a plurality of histidine residues. The coupling element may e.g. be a single cysteine at the C-terminal end. The coupling element(s) may be directly linked to the C- or N-terminal end, or it/they may be linked via a linker comprising up to 15 amino acids, such as 1-5, 1-10 or 5-10 amino acids. This stretch may also be sufficiently stable in alkaline environments not to impair the properties of the mutated protein. Therefore in an embodiment, the stretch does not contain asparagine and may not contain glutamine. A benefit of having a C-terminal cysteine is that endpoint coupling of the protein can be achieved through reaction of the cysteine thiol with an electrophilic group on a support. This provides excellent mobility of the coupled protein which is important for the binding capacity.

In a third aspect embodiments of the present invention discloses a nucleic acid encoding a polypeptide or multimer according to any embodiment disclosed above. Thus, an embodiment encompasses all forms of the present nucleic acid sequence such as the RNA and the DNA encoding the polypeptide or multimer. An embodiment embraces a vector, such as a plasmid, which in addition to the coding sequence comprises the required signal sequences for expression of the polypeptide or multimer according an embodiment. In one embodiment, the vector comprises nucleic acid encoding a multimer, wherein the separate nucleic acids encoding each unit may have homologous or heterologous DNA sequences.

In a fourth aspect embodiments of the present invention disclose an expression system, which comprises, a nucleic acid or a vector as disclosed above. The expression system may e.g. be a gram-positive or gram-negative prokaryotic host cell system, e.g. *E. coli* or *Bacillus* sp. which has been modified to express the present polypeptide or multimer. In an alternative embodiment, the expression system is a eukaryotic host cell system, such as a yeast, e.g. *Pichea pastoris* or *Saccharomyces cerevisiae*.

In a fifth aspect, an embodiment of the present invention discloses a separation matrix, wherein a plurality of polypeptides or multimers according to any embodiment disclosed above have been coupled to a solid support. Such a matrix is useful for separation of immunoglobulins or other Fc-containing proteins and, due to the improved alkali stability of the polypeptides/multimers, the matrix will withstand highly alkaline conditions during cleaning, which is essential for long-term repeated use in a bioprocess separation setting.

As the skilled person will understand, the expressed polypeptide or multimer should be purified to an appropriate extent before been immobilized to a support. Such purification methods are well known in the field, and the immobilization of protein-based ligands to supports is easily carried out using standard methods. Suitable methods and supports will be discussed below in more detail.

The solid support of the matrix according to an embodiment of the present invention can be of any suitable well-known kind. A conventional affinity separation matrix is often of organic nature and based on polymers that expose a hydrophilic surface to the aqueous media used, i.e. expose hydroxy (—OH), carboxy (—COOH), carboxamido (—CONH$_2$, possibly in N-substituted forms), amino (—NH$_2$, possibly in substituted form), oligo- or polyethylenoxy groups on their external and, if present, also on internal surfaces. The solid support can suitably be porous. The porosity can be expressed as a Kav or Kd value (the fraction of the pore volume available to a probe molecule of a particular size) measured by inverse size exclusion chromatography, e.g. according to the methods described in Gel Filtration Principles and Methods, Pharmacia LKB Biotechnology 1991, pp 6-13. By definition, both Kd and Kav values always lie within the range 0-1. The Kav value may be 0.6-0.95, e.g. 0.7-0.90 or 0.6-0.8, as measured with dextran of Mw 110 kDa as a probe molecule. A benefit of this is that the support has a large fraction of pores able to accommodate both the polypeptides/multimers of an embodiment of the present invention and immunoglobulins binding to the polypeptides/multimers and to provide mass transport of the immunoglobulins to and from the binding sites.

The polypeptides or multimers may be attached to the support via conventional coupling techniques utilising e.g. thiol, amino and/or carboxy groups present in the ligand. Bisepoxides, epichlorohydrin, CNBr, N-hydroxysuccinimide (NHS) etc are well-known coupling reagents. Between the support and the polypeptide/multimer, a molecule known as a spacer can be introduced, which improves the availability of the polypeptide/multimer and facilitates the chemical coupling of the polypeptide/multimer to the support. Alternatively, the polypeptide/multimer may be attached to the support by non-covalent bonding, such as physical adsorption or biospecific adsorption.

In some embodiments the matrix comprises 5-20, such as 5-15 mg/ml, 5-11 mg/ml or 6-11 mg/ml of the polypeptide or multimer coupled to the support. The amount of coupled polypeptide/multimer can be controlled by the concentration of polypeptide/multimer used in the coupling process, by the coupling conditions used and/or by the pore structure of the support used. As a general rule the absolute binding capacity of the matrix increases with the amount of coupled polypeptide/multimer, at least up to a point where the pores become significantly constricted by the coupled polypeptide/multimer. The relative binding capacity per mg coupled polypeptide/multimer will decrease at high coupling levels, resulting in a cost-benefit optimum within the ranges specified above.

In certain embodiments the polypeptides or multimers are coupled to the support via thioether bonds. Methods for performing such coupling are well-known in this field and easily performed by the skilled person in this field using standard techniques and equipment. Thioether bonds are flexible and stable and generally suited for use in affinity chromatography. In particular when the thioether bond is via a terminal or near-terminal cysteine residue on the polypeptide or multimer, the mobility of the coupled polypeptide/multimer is enhanced which provides improved binding capacity and binding kinetics. In some embodiments the polypeptide/multimer is coupled via a C-terminal cysteine provided on the protein as described above. This allows for efficient coupling of the cysteine thiol to electrophilic groups, e.g. epoxide groups, halohydrin groups etc. on a support, resulting in a thioether bridge coupling.

In certain embodiments the support comprises a polyhydroxy polymer, such as a polysaccharide. Examples of polysaccharides include e.g. dextran, starch, cellulose, pullulan, agar, agarose etc. Polysaccharides are inherently hydrophilic with low degrees of nonspecific interactions, they provide a high content of reactive (activatable) hydroxyl groups and they are generally stable towards alkaline cleaning solutions used in bioprocessing.

In some embodiments the support comprises agar or agarose. The supports used in an embodiment of the present invention can easily be prepared according to standard methods, such as inverse suspension gelation (S Hjertén: Biochim Biophys Acta 79(2), 393-398 (1964). Alternatively, the base matrices are commercially available products, such as SEPHAROSE™ FF (GE Healthcare). In an embodiment, which is beneficial for large-scale separations, the support has been adapted to increase its rigidity using the methods described in U.S. Pat. No. 6,602,990 or U.S. Pat. No. 7,396,467, which are hereby incorporated by reference in their entirety, and hence renders the matrix more suitable for high flow rates.

In certain embodiments the support, such as a polysaccharide or agarose support, is crosslinked, such as with hydroxyalkyl ether crosslinks. Crosslinker reagents producing such crosslinks can be e.g. epihalohydrins like epichlorohydrin, diepoxides like butanediol diglycidyl ether, allylating reagents like allyl halides or allyl glycidyl ether. Crosslinking is beneficial for the rigidity of the support and improves the chemical stability. Hydroxyalkyl ether crosslinks are alkali stable and do not cause significant nonspecific adsorption.

Alternatively, the solid support is based on synthetic polymers, such as polyvinyl alcohol, polyhydroxyalkyl acrylates, polyhydroxyalkyl methacrylates, polyacrylamides, polymethacrylamides etc. In case of hydrophobic polymers, such as matrices based on divinyl and monovinyl-substituted benzenes, the surface of the matrix is often hydrophilised to expose hydrophilic groups as defined above to a surrounding aqueous liquid. Such polymers are easily produced according to standard methods, see e.g. "Styrene based polymer supports developed by suspension polymerization" (R Arshady: Chimica e L'Industria 70(9), 70-75 (1988)). Alternatively, a commercially available product, such as SOURCE™ (GE Healthcare) is used. In another alternative, the solid support according to an embodiment comprises a support of inorganic nature, e.g. silica, zirconium oxide etc.

In yet another embodiment, the solid support is in another form such as a surface, a chip, capillaries, or a filter (e.g. a membrane or a depth filter matrix).

The shape of the matrix according to an embodiment is in the form of a porous monolith. In an alternative embodiment, the matrix is in beaded or particle form that can be porous or non-porous. Matrices in beaded or particle form can be used as a packed bed or in a suspended form. Suspended forms include those known as expanded beds and pure suspensions, in which the particles or beads are free to move. In case of monoliths, packed bed and expanded beds, the separation procedure commonly follows conventional chromatography with a concentration gradient. In case of pure suspension, batch-wise mode will be used.

In a sixth aspect, an embodiment of the present invention discloses a method of isolating an immunoglobulin, wherein a separation matrix as disclosed above is used In certain embodiments, the method comprises the steps of: contacting a liquid sample comprising an immunoglobulin with a separation matrix as disclosed above, washing the separation matrix with a washing liquid, eluting the immunoglobulin from the separation matrix with an elution liquid, and cleaning the separation matrix with a cleaning liquid.

The method may also comprise steps of before providing an affinity separation matrix according to any of the embodiments described above and providing a solution comprising an immunoglobulin and at least one other substance as a liquid sample and after recovering the eluate and optionally subjecting the eluate to further separation steps, e.g. by anion or cation exchange chromatography, multimodal chromatography and/or hydrophobic interaction chromatography. Suitable compositions of the liquid sample, the washing liquid and the elution liquid, as well as the general conditions for performing the separation are well known in the art of affinity chromatography and in particular in the art of Protein A chromatography. The liquid sample comprising an Fc-containing protein and at least one other substance may comprise host cell proteins (HCP), such as CHO cell or *E. Coli* proteins. Contents of CHO cell and *E. Coli* proteins can conveniently be determined by immunoassays directed towards these proteins, e.g. the CHO HCP or *E. Coli* HCP ELISA kits from Cygnus Technologies. The host cell proteins or CHO cell/*E. Coli* proteins may be desorbed during washing the separation matrix with a washing liquid.

The elution may be performed by using any suitable solution used for elution from Protein A media. This can e.g. be a solution or buffer with pH 5 or lower, such as pH 2.5-5 or 3-5. It can also in some cases be a solution or buffer with pH 11 or higher, such as pH 11-14 or pH 11-13. In some embodiments the elution buffer or the elution buffer gradient comprises at least one mono- di- or trifunctional carboxylic acid or salt of such a carboxylic acid. In certain embodiments the elution buffer or the elution buffer gradient comprises at least one anion species selected from the group consisting of acetate, citrate, glycine, succinate, phosphate, and formiate.

In some embodiments, the cleaning liquid is alkaline, such as with a pH of 13-14. Such solutions provide efficient cleaning of the matrix, in particular at the upper end of the interval In certain embodiments, the cleaning liquid comprises 0.1-2.0 M NaOH or KOH, such as 0.5-2.0 or 0.5-1.0 M NaOH or KOH.

In some embodiments, steps a)-d) are repeated at least 10 times, such as at least 50 times or 50-200 times.

EXAMPLES

Mutagenesis of Protein

Site-directed mutagenesis was performed by a two-step PCR using oligonucleotides coding for the asparagine replacement. As template a plasmid containing a single domain of either Z or C was used. The PCR fragments were ligated into an *E. coli* expression vector (pGO). DNA sequencing was used to verify the correct sequence of inserted fragments.

To form multimers of mutants an Acc I site located in the starting codons (GTA GAC) of the C or Z domain was used, corresponding to amino acids VD. pGO for the monomeric domain were digested with Acc I and CIP treated. Acc I sticky-ends primers were designed, specific for each variant, and two overlapping PCR products were generated from each template. The PCR products were purified and the concentration was estimated by comparing the PCR products on a 2% agarose gel. Equal amounts of the pair wise PCR products were hybridized (90° C.→25° C. in 45 min) in ligation buffer. The resulting product consists approximately to ¼ of fragments likely to be ligated into an Acc I site (correct PCR fragments and/or the digested vector). After ligation and transformation colonies were PCR screened to identify constructs containing the desired mutant. Positive clones were verified by DNA sequencing.

Construct Expression and Purification

The constructs were expressed in the bacterial periplasm by fermentation of *E. coli* K12 in standard media. After fermentation the cells were heat-treated to release the periplasm content into the media. The constructs released into the medium were recovered by microfiltration with a membrane having a 0.2 µm pore size.

Each construct, now in the permeate from the filtration step, was purified by affinity. The permeate was loaded onto a chromatography medium containing immobilized IgG. The loaded product was washed with phosphate buffered saline and eluted by lowering the pH.

The elution pool was adjusted to a neutral pH and reduced by addition of dithiothreitol. The sample was then loaded onto an anion exchanger. After a wash step the construct was eluted in a NaCl gradient to separate it from any contaminants. The elution pool was concentrated by ultrafiltration to 40-50 mg/ml. It should be noted that the successful affinity purification of a construct on an immobilized IgG medium indicates that the construct in question has a high affinity to IgG.

The purified ligands were analyzed with LC-MS to determine the purity and to ascertain that the molecular weight corresponded to the expected (based on the amino acid sequence).

Example 1

Figure 1:
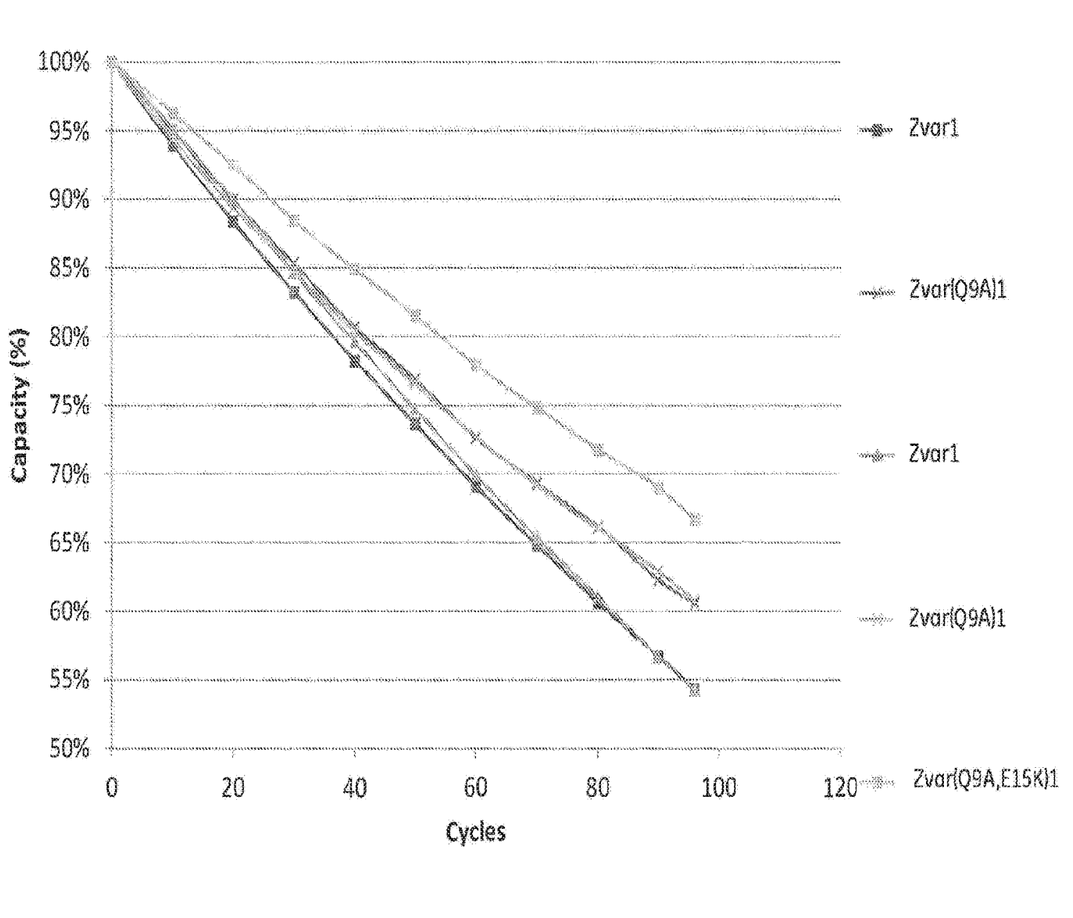
FIG. 1 shows results from Example 1 for the alkali stability of mutated and non-mutated monomeric Zvar (SEQ ID NO 4) polypeptide variants coupled to an SPR biosensor chip.

The purified monomeric ligands listed in Table 1 were immobilized on Biacore CM5 sensor chips (GE Healthcare, Sweden) in an amount sufficient to give a signal strength of about 1000 RU in a Biacore instrument (GE Healthcare, Sweden). To follow the IgG binding capacity of the immobilized surface 1 mg/ml hIgG (Gammanorm, as described above) was flowed over the chip and the signal strength was noted. The surface was then cleaned-in-place (CIP), i.e. flushed with 500 mM NaOH for 10 minutes at room temperature (22+/−2° C.). This was repeated for 96 cycles and the immobilized ligand alkaline stability was followed as the relative loss of IgG binding capacity (signal strength) after each cycle. The results are shown in FIG. 1 and Table 1 and indicate that at least the ligand Zvar(Q9A,E15K)1 has an improved alkali stability compared to the parental structure Zvar1 and that it also has an improved stability compared to the Zvar(Q9A)1 ligand.

TABLE 1

| Ligand | SEQ ID NO. | Remaining capacity after 96 cycles (%) |
|---|---|---|
| Zvar1 | 4 | 54 |
| Zvar(Q9A)1 | 7 | 61 |
| Zvar(Q9A, E15K)1 | 6 | 67 |

Example 2

The purified tetrameric ligands of Table 2 (all with an additional N-terminal cysteine) were immobilized on agarose beads using the methods described below and assessed for capacity and stability.

TABLE 2

| Ligand | SEQ ID NO. | Ligand content (mg/ml) | Initial IgG capacity Qb10 (mg/ml) | Remaining IgG capacity after 100 cycles (mg/ml) | Remaining IgG capacity after 100 cycles (%) |
|---|---|---|---|---|---|
| Zvar4 | 11 | 6.4 | 47.6 | 34.1 | 71.7 |
| Zvar(Q9A)4 | 12 | 6.3 | 46.3 | 38.8 | 83.9 |
| Zvar(Q9A, E15K)4 | 13 | 6.2 | 49.8 | 41.0 | 82.3 |

Activation

The base matrix used was rigid cross-linked agarose beads of 85 micrometers (volume-weighted) median diameter, prepared according to the methods of U.S. Pat. No. 6,602,990 and with a pore size corresponding to an inverse gel filtration chromatography Kav value of 0.70 for dextran of Mw 110 kDa, according to the methods described in Gel Filtration Principles and Methods, Pharmacia LKB Biotechnology 1991, pp 6-13.

25 mL (g) of drained base matrix, 10.0 mL distilled water and 2.02 g NaOH (s) was mixed in a 100 mL flask with mechanical stirring for 10 min at 25° C. 4.0 mL of epichlorohydrin was added and the reaction progressed for 2 hours. The activated gel was washed with 10 gel sediment volumes (GV) of water.

Coupling

To 20 mL of ligand solution (50 mg/mL) in a 50 ml Falcon tube, 169 mg NaHCO$_3$, 21 mg Na$_2$CO$_3$, 175 mg NaCl and 7 mg EDTA, was added. The Falcon tube was placed on a roller table for 5-10 min, and then 77 mg of DTE was added. Reduction proceeded for >45 min. The ligand solution was then desalted on a PD10 column packed with Sephadex G-25. The ligand content in the desalted solution was determined by measuring the 276 nm UV absorption.

The activated gel was washed with 3-5 GV {0.1 M phosphate/1 mM EDTA pH 8.6} and the ligand was then coupled according to the method described in U.S. Pat. No. 6,399,750. All buffers used in the experiments had been degassed by nitrogen gas for at least 5-10 min. The ligand content of the gels could be controlled by varying the concentration of the ligand solution.

After immobilization the gels were washed 3×GV with distilled water. The gels+1 GV {0.1 M phosphate/1 mM EDTA/10% thioglycerol pH 8.6} was mixed and the tubes were left in a shaking table at room temperature overnight. The gels were then washed alternately with 3×GV {0.1 M TRIS/0.15 M NaCl pH 8.6} and 0.5 M HAc and then 8-10×GV with distilled water. Gel samples were sent to an external laboratory for amino acid analysis and the ligand content (mg/ml gel) was calculated from the total amino acid content.

2 ml of resin was packed in TRICORN™ 5 100 columns.

Protein

Gammanorm 165 mg/ml (Octapharma), diluted to 1 mg/ml in Equilibration buffer.

Equilibration Buffer

APB Phosphate buffer 20 mM+0.15 M NaCl, pH 7.4 (Elsichrom AB)

Adsorption Buffer

APB Phosphate buffer 20 mM+0.15 M NaCl, pH 7.4 (Elsichrom AB).

Elution Buffers

Citrate buffer 0.1 M, pH 6.
Citrate buffer 0.1 M, pH 3.

CIP 0.5 M NaOH

The breakthrough capacity was determined with an ÄKTAExplorer 10 system at a residence time of 2.4 minutes.

Equilibration buffer was run through the bypass column until a stable baseline was obtained. This was done prior to auto zeroing. Sample was applied to the column until a 100% UV signal was obtained. Then, equilibration buffer was applied again until a stable baseline was obtained.

Sample was loaded onto the column until a UV signal of 85% of maximum absorbance was reached. The column was then washed with equilibration buffer until a UV signal of 20% of maximum absorbance at flow rate 0.5 ml/min. The protein was eluted with a linear gradient over 10 column volumes starting at pH 6.0 and ending at pH 3.0 at a flow rate of 0.5 ml/min. Then the column was cleaned with 0.1M NaOH at flow rate 0.5 ml/min and re-equilibrated with equilibration buffer prior to cleaning with 20% ethanol. The last step was to check the sample concentration by loading sample through the bypass column until a 100% UV signal was obtained.

For calculation of breakthrough capacity at 10%, the equation below was used. That is the amount of IgG that is loaded onto the column until the concentration of IgG in the column effluent is 10% of the IgG concentration in the feed.

$$q_{10\%} = \frac{C_0}{V_c}\left[V_{app} - V_{sys} - \int_{V_{sys}}^{V_{app}} \frac{A(V) - A_{sub}}{A_{100\%} - A_{sub}} * dv\right]$$

$A_{100\%}$=100% UV signal;
$A_{sub}$=absorbance contribution from non-binding IgG subclass;
$A(V)$=absorbance at a given applied volume;
$V_c$=column volume;
$V_{app}$=volume applied until 10% breakthrough;
$V_{sys}$=system dead volume;
$C_0$=feed concentration.

The dynamic binding capacity (DBC) at 10% breakthrough was calculated and the appearance of the curve was studied. The curve was also studied regarding binding, elution and CIP peak. The dynamic binding capacity (DBC) was calculated for 10 and 80% breakthrough.

The 10% breakthrough DBC (Qb10) was determined both before and after repeated exposures to alkaline cleaning solutions. Each cycle included a CIP step with 0.5 M NaOH pumped through the column at a rate of 5 microliters/min, resulting in 10 min exposure time per cycle. The exposure took place at room temperature (22+/−2° C.). Table 2 shows the remaining capacity after 100 cycles (i.e. 1000 min cumulative exposure time to 0.5 M NaOH), both in absolute numbers and relative to the initial capacity.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

---

The invention claimed is:

1. A separation matrix, comprising a plurality of polypeptides or multimers of the polypeptides coupled to a solid support, wherein the polypeptide comprises the amino acid sequence selected from the group consisting of SEQ ID NOS: 6-10, 12, 13, or a combination thereof.

2. The separation matrix of claim 1, wherein the polypeptides or multimers thereof have been coupled to the solid support via thioether bonds.

3. The separation matrix of claim 1, wherein the solid support is a polysaccharide.

4. A method of isolating an immunoglobulin using the separation matrix of claim 1, the method comprising the steps of: a) contacting a liquid sample comprising an immunoglobulin with the separation matrix of claim 1, b) washing said separation matrix with a washing liquid, c) eluting the immunoglobulin from the separation matrix with an elution liquid, and d) cleaning the separation matrix with a cleaning liquid.

5. The method of claim 4, wherein the cleaning liquid is alkaline having a pH of 13-14.

6. The method of claim 4, wherein the cleaning liquid comprises 0.1-1.0 M NaOH or KOH.

7. The method of claim 4, wherein steps a)-d) are repeated at least 10 times.

8. The separation matrix of claim 1, wherein the polypeptide comprises the amino acid sequence of SEQ ID NO: 6.

9. The separation matrix of claim 1, wherein the polypeptide comprises the amino acid sequence of SEQ ID NO: 7.

10. The separation matrix of claim 1, wherein the polypeptide comprises the amino acid sequence of SEQ ID NO: 8.

11. The separation matrix of claim 1, wherein the polypeptide comprises the amino acid sequence of SEQ ID NO: 9.

12. The separation matrix of claim 1, wherein the polypeptide comprises the amino acid sequence of SEQ ID NO: 10.

13. The separation matrix of claim 1, wherein the polypeptide comprises the amino acid sequence of SEQ ID NO: 12.

14. The separation matrix of claim 1, wherein the polypeptide comprises the amino acid sequence of SEQ ID NO: 13.

15. The separation matrix of claim 1, wherein the polypeptide is the amino acid multimer with each monomer of the multimer comprising a sequence of any one of SEQ ID NOS: 6-10, 12, or 13.

16. The separation matrix of claim 1, wherein the polypeptide is the amino acid multimer with each monomer comprising a sequence of SEQ ID NO: 6.

17. The separation matrix of claim 1, wherein polypeptide is the amino acid multimer with each monomer comprising a sequence of SEQ ID NO: 7.

18. The separation matrix of claim 1, wherein the polypeptide is the amino acid multimer with each monomer comprising a sequence of SEQ ID NO: 8.

19. The separation matrix of claim 1, wherein the polypeptide is the amino acid multimer with each monomer comprising a sequence of SEQ ID NO: 9.

20. The separation matrix of claim 1, wherein the polypeptide is the amino acid multimer with each monomer comprising a sequence of SEQ ID NO: 10.

21. The separation matrix of claim 1, wherein the polypeptide is a multimer with each monomer comprising a sequence of SEQ ID NO: 12.

22. The separation matrix of claim 1, wherein the polypeptide is a multimer with each monomer comprising a sequence of SEQ ID NO: 13.

23. The separation matrix of claim 1, wherein the multimer comprises a plurality of the polypeptide units linked by elements comprising up to 15 amino acids.

24. The separation matrix of claim 1, wherein the multimer is a dimer, trimer, tetramer, pentamer or hexamer.

25. The separation matrix of claim 1, further comprising at the C-terminal or N-terminal of the polypeptide or multimer of the polypeptide one or more coupling element to couple the polypeptide to the support, wherein the coupling element is selected from the group consisting of a cysteine residue, a plurality of lysine residues and a plurality of histidine residues.

* * * * *